(12) United States Patent
Velaparthi

(10) Patent No.: US 8,148,522 B2
(45) Date of Patent: *Apr. 3, 2012

(54) INTERMEDIATE USEFUL IN PREPARING CERTAIN PYRROLOTRIAZINE COMPOUNDS AND A PROCESS FOR MAKING THE INTERMEDIATE

(75) Inventor: Upender Velaparthi, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/521,136

(22) PCT Filed: Jan. 2, 2008

(86) PCT No.: PCT/US2008/050005
§ 371 (c)(1),
(2), (4) Date: Sep. 15, 2009

(87) PCT Pub. No.: WO2008/083398
PCT Pub. Date: Jul. 10, 2008

(65) Prior Publication Data
US 2011/0071288 A1    Mar. 24, 2011

Related U.S. Application Data

(60) Provisional application No. 60/883,105, filed on Jan. 2, 2007.

(51) Int. Cl.
*C07D 487/04* (2006.01)
*A61K 31/53* (2006.01)
(52) U.S. Cl. ....................... 544/183; 514/243
(58) Field of Classification Search .................. 544/183; 514/243

See application file for complete search history.

(56) References Cited

U.S. PATENT DOCUMENTS

| 7,232,901 | B2 * | 6/2007 | Mastalerz et al. | ............ 544/183 |
| 7,619,083 | B2 * | 11/2009 | Mastalerz et al. | ............ 544/183 |
| 2006/0084650 | A1 | 4/2006 | Dong et al. | |
| 2007/0004734 | A1 * | 1/2007 | Mastalerz et al. | ............ 514/243 |
| 2007/0015760 | A1 | 1/2007 | Mastalerz et al. | |

FOREIGN PATENT DOCUMENTS

WO   WO 2004/013145   2/2004

* cited by examiner

*Primary Examiner* — Venkataraman Balasubramanian
(74) *Attorney, Agent, or Firm* — Elliott Korsen

(57) ABSTRACT

The invention relates to 2,4-dibromoropyrrolo[1,2-f][1,2,4] triazine, which is an intermediate useful in preparing 2,4-disubstituted pyrrolotriazine compounds, and a process for preparing the intermediate.

5 Claims, No Drawings

INTERMEDIATE USEFUL IN PREPARING CERTAIN PYRROLOTRIAZINE COMPOUNDS AND A PROCESS FOR MAKING THE INTERMEDIATE

FIELD OF THE INVENTION

The invention generally relates to 2,4-dibromopyrrolo[1,2-f][1,2,4]triazine, which is an intermediate useful in preparing 2,4-disubstituted pyrrolotriazine compounds, and a process for making said intermediate. The compound of the invention is an intermediate used in the preparation of compounds that may be useful for the treatment of cancer.

BACKGROUND OF THE INVENTION

Hyperproliferative diseases, such as, cancer are generally characterized by uncontrolled cellular proliferation and/or disruption in programmed cell death. Uncontrolled cellular proliferation is often caused by genetic damage to cellular pathways responsible for regulating cellular functions, such as, metabolism, cell cycle progression, cell adhesion, vascular function, apoptosis, and angiogenesis. As a result, one approach utilized in treating hyperproliferative diseases has involved targeting at least one protein involved in regulating cellular functions.

The protein kinase(s) (PK(s)) are a class of proteins that have been identified as playing an important role in regulating cellular functions. Indeed, many diseases are associated with abnormal cellular responses triggered by PK-mediated events. Such diseases include, but are not limited to, for example, autoimmune diseases, bone diseases, inflammatory diseases/disorders, metabolic diseases, neurological and neurodegenerative diseases, cancer, cardiovascular diseases, allergies and asthma, Alzheimer's disease, and hormone related diseases.

The PKs are a large and diverse group of enzymes that can be divided into groups based on the particular amino acids (serine/threonine, tyrosine, lysine, and histidine) targeted by each PK. For example, receptor and non-receptor tyrosine kinases target tyrosine, whereas cyclin dependent kinases (CDKs) and mitogen activated protein kinases (MAPKs) target both tyrosine and serine/threonine.

Exemplary PKs include, but are not limited to, receptor tyrosine kinases (RTKs); non-receptor tyrosine kinases or cellular tyrosine kinases (CTKs); serine/threonine kinases (STKs); cyclin dependent kinases (CDKs); and mitogen-activated protein kinases (MAPKs).

Exemplary RTKs include, but are not limited to, type III RTKs, such as, Flt3; "HER" RTKs, such as, epithelial growth factor receptor (EGFR), HER2, HER3, and HER4; C-MET; insulin receptor (IR); insulin-like growth factor 1 receptor (IGF-IR) and its ligands IGF-1 and IGF-2; insulin receptor related receptor (IRR); platelet derived growth factor receptors (PDGFRs), such as, PDGFRα, PDGFRβ, CSFIR, c-kit, and c-fms; fetus liver kinases (flks), such as, kinase insert domain-receptor fetal liver kinase-1 (KDR/FLK-1, VEGF-R2), flk-1R, flk-4, and fms-like tyrosine kinase 1 (flt-1); fibroblast growth factor (FGF) receptors, such as, FGFR1, FGFR2, FGFR3, and FGFR4 and FGF ligands, such as, FGF 1, FGF2, FGF3, FGF4, FGF5, FGF6, and FGF7; vascular endothelial growth factor receptors (VEGFRs), such as, VEGFR1, VEGFR2, and VEGFR3; Tie receptors, such as fro example, Tie2; and Trk receptors, such as, TrkA, TrkB, and TrkC. For a more detailed discussion of RTKs, see Plowman et al., *KN&P*, 7(6):334-339 (1994).

Exemplary CTKs include, but are not limited to, Src kinases, such as, Src, Yes, Fyn, Lyn, Lck, Blk, Hck, Fgr, and Yrk; Frk kinases; Btk kinases; Csk kinases; Abl kinases; ZAP70 kinases; Fes kinases; Fps kinases; Fak kinases; Jak kinases; Ack kinases; and Kak kinases. For a more detailed discussion of known CTKs, see Bolen, *Oncogene*, 8:2025-2031 (1993).

Exemplary STKs include, but are not limited to, p90 ribosomal S6 kinases (RSKs), such as, RSK1/p90Rsk, RSK2, RSK3, and RSK4; checkpoint protein kinases, such as, CHK1 and CHK2; Aurora kinases, such as, aurora-A, aurora-B, and aurora-C; and Glycogen synthase kinase 3 (GSK3).

Exemplary CDKs include, but are not limited to, CDK1; CDK2; CDK4; CDK5; CDK6 and CDK 7; and cell division control 2 proteins (CDC2);

Exemplary MAPKs include, but are not limited to, MAPK 1 (ERK); MAPK3; MAPK7; MAPK 8 (JNK1); MAPK 14 (p38α); MAPK 10; JNK 3α protein kinase; stress-activated protein kinase YNK 2; and MAPK 14.

In view of the link between PK-related cellular activities and a wide variety of human disorders, including, cancer, and the discovery that certain pyrrolotriazine-containing compounds exhibit inhibitory activity of at least one PK, such pyrrolotriazine-containing compounds were found to be useful in treating conditions associated with abnormal PK activity.

2,4-Dichloropyrrolo[1,2-f][1,2,4]triazine, as an intermediate for the preparation of certain pyrrolotriazine compounds, is disclosed in U.S. Ser. No. 11/426,707, filed Jun. 27, 2006. 2,4-Disubstituted pyrrolotriazine compounds are disclosed in the following patent applications, U.S. Ser. No. 11/773,466, U.S. Ser. No. 11/835,456, U.S. Ser. No. 11/835,469, and PCT/US2007/083436.

SUMMARY OF THE INVENTION

The invention relates to the compound of formula I,

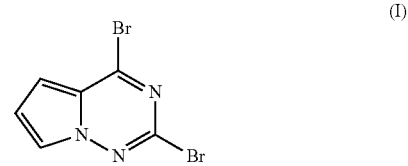

(I)

or a pharmaceutically acceptable salt thereof.

Further described herein is a process for preparing the compound of Formula I or a pharmaceutically acceptable salt thereof comprising contacting the compound of formula V,

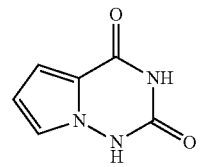

or a pharmaceutically acceptable salt thereof, with a brominating agent to form a mixture, and heating the mixture to form the compound of formula I, or a pharmaceutically acceptable salt thereof.

DETAILED DESCRIPTION OF THE INVENTION

The features and advantages of the invention may be more readily understood by those of ordinary skill in the art upon reading the following detailed description.

The compound of Formula I can also form salt(s). Exemplary acidic salt(s) of Formula I can form with inorganic and/or organic acids include, but are not limited to, for example, acetates, such as are formed with acetic or trihaloacetic acid; adipates; alginates; ascorbates; aspartates; benzoates; benzenesulfonates; bisulfates; borates; butyrates; citrates; camphorates; camphorsulfonates; cyclopentanepropionates; digluconates; dodecylsulfates; ethanesulfonates; fumarates; glucoheptanoates; glycerophosphates; hemisulfates; heptanoates; hexanoates; hydrochlorides; hydrobromides; hydroiodides; hydroxyethanesulfonates, such as, for example, 2-hydroxyethanesulfonates; lactates; maleates; methanesulfonates; naphthalenesulfonates, such as, for example, 2-naphthalenesulfonates; nicotinates; nitrates; oxalates; pectinates; persulfates; phenylpropionates, such as, for example, 3-phenylpropionates; phosphates; picrates; pivalates; propionates; salicylates; succinates; sulfates, such as, for example, are formed with sulfuric acid; sulfonates; tartrates; thiocyanates; and toluenesulfonates, such as, for example, tosylates and undecanoates. Such salts can be formed in accordance with methods known to a person of ordinary skill in the art.

Exemplary basic salt(s) that compounds of Formula I can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), and aralkyl halides (e.g. benzyl and phenethyl bromides) to quaternize basic nitrogen-containing groups. Such salts can be formed in accordance with methods known to a person of ordinary skill in the art.

In general, the compound of formula I can be prepared in accordance with schemes 1 and 2 and the general knowledge of one skilled in the art. Scheme 1 shows the preparation of the dione intermediate which is disclosed and claimed in U.S. Ser. No. 11/475,828 filed Jun. 27, 2006, which is incorporated herein in its entirety. Scheme 2 shows the reaction of the dione with a suitable brominating agent to afford Compound I of the invention.

Scheme 1

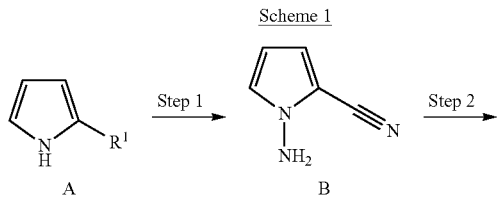

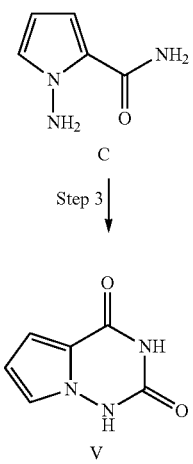

Step 1

Compound B can be prepared by contacting an appropriately substituted compound A with an aminating agent, such as for example, hydroxylamino-O-sulfonic acid ($H_2NOSO_3H$) when $R^1$ is CHO and monochloramine ($NH_2Cl$) when $R^1$ is CN in the presence of a base, such as, for example, potassium t-butoxide or an aqueous solution of potassium hydroxide. Step 1 can be carried out in accordance with methods readily known to a person of ordinary skill in the art including, but not limited to, for example, the methods disclosed in the Journal of Heterocyclic Chemistry, volume 31, page 781 (1994) and/or the Journal of Organic Chemistry, volume 69, page 1368 (2004).

Step 2

Compound C can be prepared by converting the nitrile group of compound B to a carboxamide. The nitrile group can be converted to the carboxamide in accordance with any method readily known to a person of ordinary skill in the art. For example, compound B can be contacted with an aqueous solution of a base, such as, for example, potassium hydroxide to partially hydrolyze the nitrite group and form a carboxamide group. An appropriately substituted compound C can be produced in accordance with methods readily known to a person of ordinary skill in the art including, but not limited to, for example, the methods disclosed in the Journal of Heterocyclic Chemistry, volume 31, page 781 (1994) and/or R.C. Larock, Comprehensive Organic Transformations, $2^{nd}$ edition, page, 1988, Wilcy-VCH, New York (1999).

Step 3

Compound V can be prepared by contacting an appropriately substituted compound C with a reagent, such as, for example, ethyl chloroformate in the presence of an appropriate base, such as, for example, pyridine, and a solvent, such as, for example, dioxane. In one embodiment, compound V is produced by heating the mixture of compound C, reagent, base, and solvent at an acceptable temperature and for an acceptable period of time to produce compound V. A person of ordinary skill in the art is readily familiar with and/or able to determine the temperature and period of time at which the mixture of compound C, reagent, base, and solvent may be heated to produce formula V compound.

Scheme 2

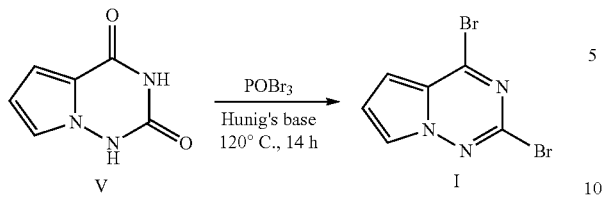

Step 1

Compound I can be prepared by heating compound V with a brominating agent, such as, for example, phosphorus oxybromide in the presence of a Hunig's base, such as, for example, diisopropylethylamine and a solvent. A person of ordinary skill in the art is readily familiar with and/or able to determine the temperature and period of time at which compound V and brominating agent may be heated in the presence of base and solvent to produce compound I.

EXAMPLES

The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth hereinbelow, but rather defined by the claims appended hereto.

All temperatures are in degrees Celsius (° C.) unless indicated otherwise herein.

Example 1

2,4-Dibromopyrrolo[1,2-f][1,2,4]triazine (1)

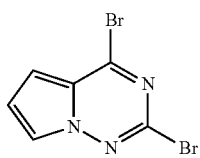

A mixture of pyrrolo[2,1-f][1,2,4]triazine-2,4(1H,3H)-dione (4.3 gm, 28.47 mmol), POBr$_3$ (24.5 gm, 85.43 mmol) and diisopropylethylamine (7.36 gm, 56.95 mmol) was heated at 120° C. for 14 hr. After cooling to room temperature, the syrup was poured into ice. A sat. aq. solution of NaHCO$_3$ was slowly added with stirring until the pH of the mixture reaches 7. The dark aqueous phase was then extracted with methylene chloride. The combined organic phases were washed with brine, dried (Na$_2$SO$_4$), and the solvent was evaporated. Silica gel column chromatography (elution with 100% CH$_2$Cl$_2$) gave 4.0 gm of 2,4-dibromopyrrolo[1,2-f][1,2,4]triazine (1) (52% yield) as a solid. $^1$H NMR (CDCl$_3$): 6.96 (m, 1H), 7.03 (m, 1H), 7.85 (m, 1H); MS: 275 (M+H)$^+$; and HPLC ret. time: 1.86 min. (Phenomenex-Luna S 10: 4.6×50 mm column, 2 min gradient, 4 mL/min).

I claim:
1. A compound of the formula

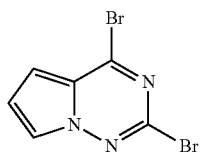

or a pharmaceutically acceptable salt thereof.

2. A process for preparing a compound of formula I,

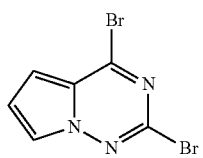

or a pharmaceutically acceptable salt thereof, comprising:
contacting a compound of formula V,

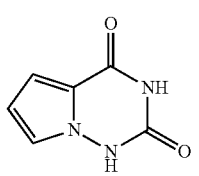

or a pharmaceutically acceptable salt thereof, with a brominating agent to form a mixture, and heating the mixture to form a compound of formula I, or a pharmaceutically acceptable salt thereof.

3. The process according to claim 2, wherein the compound V is contacted with the brominating agent in the presence of a base and a solvent to form the mixture.

4. The process according to claim 3, wherein the brominating agent is phosphorous oxybromide and the base is diisopropylethylamine.

5. A process for preparing a compound of formula I,

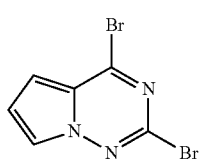

or a pharmaceutically acceptable salt thereof, comprising:
(a) contacting a compound of formula A,

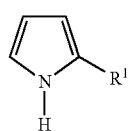

wherein
R[1] is CHO or CN;
with an aminating agent in the presence of a base to form a compound of formula B,

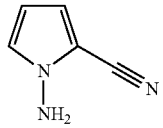

B (b) converting the compound of formula B to the compound of formula C,

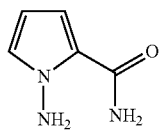

C and (c) contacting the formula C compound with a reagent which is ethylformate in the presence of a base and a solvent to form the compound of formula V,

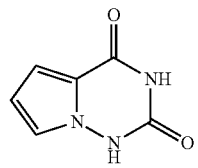

V or a pharmaceutically acceptable salt thereof; and (d) contacting the compound V with a brominating agent to form a mixture, and heating the mixture to form the compound of formula I, or a pharmaceutically acceptable salt thereof.

* * * * *